United States Patent
Lamego

(10) Patent No.: US 8,374,665 B2
(45) Date of Patent: Feb. 12, 2013

(54) TISSUE PROFILE WELLNESS MONITOR

(75) Inventor: Marcelo Lamego, Rancho Santa Margarita, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 1301 days.

(21) Appl. No.: 12/106,969

(22) Filed: Apr. 21, 2008

(65) Prior Publication Data

US 2008/0262325 A1 Oct. 23, 2008

Related U.S. Application Data

(60) Provisional application No. 60/925,811, filed on Apr. 21, 2007.

(51) Int. Cl.
*A61B 5/1455* (2006.01)
(52) U.S. Cl. .................................. 600/322; 600/324
(58) Field of Classification Search .................. 600/310, 600/322, 323, 324
See application file for complete search history.

(56) References Cited

U.S. PATENT DOCUMENTS

| | | | |
|---|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |

(Continued)

*Primary Examiner* — Eric Winakur
(74) *Attorney, Agent, or Firm* — Knobbe Martens Olson & Bear LLP

(57) ABSTRACT

A tissue profile wellness monitor measures a physiological parameter, generates a tissue profile, defines limits and indicates when the tissue profile exceeds the defined limits. The physiological parameter is responsive to multiple wavelengths of optical radiation after attenuation by constituents of pulsatile blood flowing within a tissue site. The tissue profile is responsive to the physiological parameter. The limits are defined for at least a portion of the tissue profile.

16 Claims, 5 Drawing Sheets

U.S. PATENT DOCUMENTS

| | | |
|---|---|---|
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,675,031 B1 * | 1/2004 | Porges et al. .................. 600/322 |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |

| | | |
|---|---|---|
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 2006/0211925 A1* | 9/2006 | Lamego et al. ............... 600/310 |

* cited by examiner

TISSUE PROFILE WELLNESS MONITOR

PRIORITY CLAIM TO RELATED PROVISIONAL APPLICATIONS

The present application claims priority benefit under 35 U.S.C. §119(e) of U.S. Provisional Application Ser. No. 60/925,811, filed Apr. 21, 2007, entitled "TISSUE PROFILE WELLNESS MONITOR," which is incorporated herein by reference.

BACKGROUND OF THE INVENTION

Spectroscopy is a common technique for measuring the concentration of organic and some inorganic constituents of a solution. The theoretical basis of this technique is the Beer-Lambert law, which states that the concentration $c_i$ of an absorbent in solution can be determined by the intensity of light transmitted through the solution, knowing the pathlength $d_\lambda$, the intensity of the incident light $I_{0,\lambda}$, and the extinction coefficient $\epsilon_{i,\lambda}$ at a particular wavelength $\lambda$. In generalized form, the Beer-Lambert law is expressed as:

$$I_\lambda = I_{0,\lambda} e^{-d_\lambda \cdot \mu_{a,\lambda}} \quad (1)$$

$$\mu_{a,\lambda} = \sum_{i=1}^{n} \epsilon_{i,\lambda} \cdot c_i \quad (2)$$

where $\mu_{a,\lambda}$ is the bulk absorption coefficient and represents the probability of absorption per unit length. The minimum number of discrete wavelengths that are required to solve EQS. 1-2 are the number of significant absorbers that are present in the solution.

A practical application of this technique is pulse oximetry, which utilizes a noninvasive sensor to measure oxygen saturation ($SpO_2$) and pulse rate. The sensor has light emitting diodes (LEDs) that transmit optical radiation of red and infrared wavelengths into a tissue site and a detector that responds to the intensity of the optical radiation after attenuation by pulsatile arterial blood flowing within the tissue site. Based on this response, a processor determines measurements for $SPO_2$ and pulse rate, and outputs representative plethysmographic waveforms. Thus, "pulse oximetry" as used herein encompasses its broad ordinary meaning known to one of skill in the art, which includes at least those noninvasive procedures for measuring parameters of circulating blood through spectroscopy. Moreover, "plethysmograph" as used herein encompasses its broad ordinary meaning known to one of skill in the art, which includes at least data representative of a change in the absorption of particular wavelengths of light as a function of the changes in body tissue resulting from pulsing blood.

Pulse oximeters capable of reading through motion induced noise are available from Masimo Corporation ("Masimo") of Irvine, Calif. Moreover, portable and other oximeters capable of reading through motion induced noise are disclosed in at least U.S. Pat. Nos. 6,770,028, 6,658,276, 6,584,336, 6,263,222, 6,157,850, 5,769,785, and 5,632,272, which are owned by Masimo, and are incorporated by reference herein. Such reading through motion oximeters have gained rapid acceptance in a wide variety of medical applications, including surgical wards, intensive care and neonatal units, general wards, home care, physical training, and virtually all type of monitoring scenarios.

FIG. 1 illustrates an absorption graph 100 having a dimensionless vertical axis 101 of relative light absorption and a horizontal axis 102 of transmitted wavelength in nm. Shown is a plot of $HbO_2$ absorption 110 and Hb absorption 120 versus wavelength, both normalized to the absorption at 800 nm. At red and near IR wavelengths below 970 nm, where water has a significant peak, Hb and $HbO_2$ are the only significant absorbers normally present in the blood. Thus, typically only two wavelengths are needed to resolve the concentrations of Hb and $HbO_2$, e.g. a red (RD) wavelength at 660 nm and an infrared (IR) wavelength at 940 nm. In particular, $SPO_2$ is computed based upon a red ratio $Red_{AC}/Red_{DC}$ and an IR ratio $IR_{AC}/IR_{DC}$, which are the AC detector response magnitude at a particular wavelength normalized by the DC detector response at that wavelength. The normalization by the DC detector response reduces measurement sensitivity to variations in tissue thickness, emitter intensity and detector sensitivity, for example. The AC detector response is a plethysmograph, as described above. Thus, the red and IR ratios can be denoted as $NP_{RD}$ and $NP_{IR}$ respectively, where NP stands for "normalized plethysmograph." In pulse oximetry, oxygen saturation is calculated from the ratio $NP_{RD}/NP_{IR}$.

SUMMARY OF THE INVENTION

Oxygen saturation is a very useful physiological parameter for indicating the cardiovascular status of a patient, but allows healthcare providers only a few minutes warning that a patient is potentially having a medical crisis. A wellness indicator advantageously monitors changes in a patient's "tissue profile" so as to provide an advance warning of a deteriorating medical condition. This tissue profile is provided by a multiple wavelength sensor and a noninvasive multi-parameter patient monitor, which make blood absorption measurements at more than a red wavelength and an IR wavelength of conventional pulse oximetry. In one embodiment, described below, blood absorption measurements are made at eight wavelengths. Advantageously, this rich wavelength data characterizes a tissue site over a wavelength spectrum.

FIG. 2 illustrates an example of a tissue profile. In this example, the sensor emits eight wavelengths (610, 620, 630, 655, 700, 720, 800 and 905 nm). A tissue profile graph 200 has a NP ratio axis 201 and a wavelength axis 202, where the NP ratios are of the form $NP_{\lambda,1}/NP_{\lambda,2}$. This is a generalization to multiple wavelengths of the ratio $NP_{RD}/NP_{IR}$ described above for two (red and IR) wavelengths. In order to provide a common scale for these NP ratios, the ratios are calculated with respect to a reference wavelength, $\lambda r$, which may be any of the available wavelengths. Thus, the plotted NP ratios 210 are denoted $NP_{\lambda,r'}/NP_{\lambda,r}$. Note that the NP ratio at the reference wavelength is $NP_{\lambda,r}/NP_{\lambda,r}=1$, which is 700 nm in this example. In this example, a tissue profile 210 is plotted for $SPO_2=97\%$.

Not surprisingly, the tissue profile 210 has the same general shape as the absorption curves 110, 120 of FIG. 1. In particular, the AC component of the detector signal relative to the DC component (NP) for a specific wavelength is proportional to the light absorption at that wavelength. Thus, the NP ratio magnitudes and hence the points along a tissue profile curve are proportional to absorption. Assuming negligible abnormal Hb species, if $SPO_2$ is close to 100%, most of the absorption is due to $HbO_2$ and, accordingly, the tissue profile is shaped closely to the $HbO_2$ absorption curve. As $SpO_2$ decreases from 100%, the tissue profile shape is increasing influenced by the shape of the Hb absorption curve.

In one embodiment, the tissue profile 210 consists solely of the measured NP ratios at the sensor wavelengths, i.e. a finite set of discrete values. In another embodiment, the tissue profile 210 consists of the measured NP ratios and defined NP ratio values between the sensor wavelengths, which are based upon tissue absorption characteristics. That is, the tissue profile 210 is a curve defined over a continuous range of wavelengths, including the sensor wavelengths. Although described above with respect to NP ratios derived from the AC component of the detector signal, a DC tissue profile may also be defined and applied to patient monitoring, as described below.

A tissue profile or tissue characterization is described in U.S. patent application Ser. No. 11/367,034, filed Mar. 1, 2006 entitled Physiological Parameter Confidence Measure; a multiple wavelength sensor is disclosed in U.S. patent application Ser. No. 11/367,013, filed Mar. 1, 2006 entitled Multiple Wavelength Sensor Emitters; and a multi-parameter patient monitor is disclosed in U.S. patent application Ser. No. 11/367,033, filed Mar. 1, 2006 entitled Noninvasive Multi-Parameter Patient Monitor, all of the aforementioned applications are assigned to Masimo Laboratories, Inc., Irvine, Calif. and all are incorporated by reference herein.

One aspect of a tissue profile wellness monitor comprises generating a tissue profile, predetermining rules and applying the rules to the tissue profile. The tissue profile is responsive to absorption of emitted wavelengths of optical radiation by pulsatile blood flowing within a tissue site. The rules are used to evaluate at least a portion of the tissue profile. A patient condition is indicated according to the applied rules.

Another aspect of a tissue profile wellness monitor comprises measuring a normalized plethysmograph (NP) to generate a tissue profile, testing the tissue profile and outputting the test results. The NP is measured at each of multiple wavelengths of optical radiation, and the NP is responsive to attenuation of the optical radiation by constituents of pulsatile blood flowing within a tissue site illuminated by the optical radiation. The tissue profile is tested against predetermined rules. The test results are output as at least one of a display, alarm, diagnostic and control.

A further aspect of a tissue profile wellness monitor comprises measuring a physiological parameter, generating a tissue profile, defining limits and indicating when the tissue profile exceeds the defined limits. The physiological parameter is responsive to multiple wavelengths of optical radiation after attenuation by constituents of pulsatile blood flowing within a tissue site. The tissue profile is responsive to the physiological parameter. The limits are defined for at least a portion of the tissue profile.

DETAILED DESCRIPTION OF THE PREFERRED EMBODIMENTS

Figure 3:
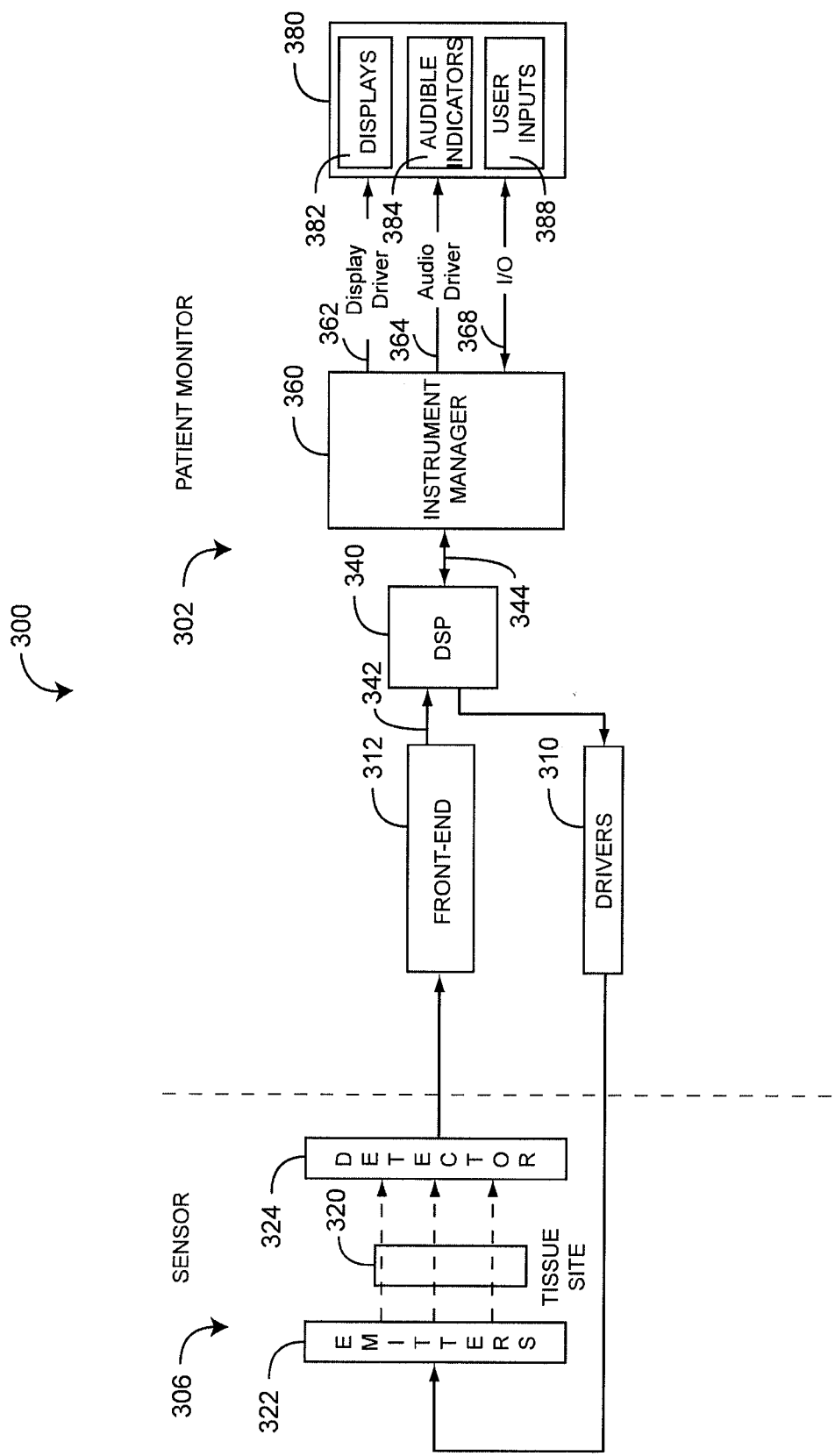
FIG. 3 is a general block diagram of a patient monitoring system embodiment that implements a tissue profile wellness monitor.

FIG. 3 illustrates a patient monitoring system 300, which generates NP ratios and blood parameter measurements, such as $SPO_2$, HbCO and HbMet, accordingly. The patient monitoring system is advantageously adapted as a tissue profile wellness monitor, as described below. The patient monitoring system 300 has a patient monitor 302 and a sensor 306. The sensor 306 attaches to a tissue site 320 and includes a plurality of emitters 322 capable of irradiating the tissue site 320 with differing wavelengths of light, perhaps including the red and infrared wavelengths utilized in pulse oximeters. The sensor 306 also includes one or more detectors 324 capable of detecting the light after attenuation by the tissue site 320. A multiple wavelength sensor is disclosed in U.S. App. No. 11,367,013, filed on Mar. 1, 2006, titled Multiple Wavelength Sensor Emitters, cited above. Multiple wavelength sensors, such as Rainbow™-brand adhesive and reusable sensors are available from Masimo Corporation, Irvine, Calif.

As shown in FIG. 3, the patient monitor 302 communicates with the sensor 306 to receive one or more intensity signals indicative of one or more physiological parameters. Drivers 310 convert digital control signals into analog drive signals capable of driving the sensor emitters 322. A front-end 312 converts composite analog intensity signal(s) from light sensitive detector(s) 324 into digital data 342 input to the DSP 340. The DSP 340 may comprise a wide variety of data and/or signal processors capable of executing programs for determining physiological parameters from input data. In an embodiment, the DSP 340 executes the processors 610, 620, 630 (FIG. 6), described below.

The instrument manager 360 may comprise one or more microcontrollers providing system management, such as monitoring the activity of the DSP 340. The instrument manager 360 also has an input/output (I/O) port 368 that provides a user and/or device interface for communicating with the monitor 302. In an embodiment, the I/O port 368 provides threshold settings via a user keypad, network, computer or similar device, as described below.

Also shown in FIG. 3 are one or more user I/O devices 380 including displays 382, audible indicators 384 and user inputs 388. The displays 382 are capable of displaying indicia representative of calculated physiological parameters such as one or more of a pulse rate (PR), plethysmograph (pleth), perfusion index (PI), signal quality and values of blood constituents in body tissue, including for example, oxygen saturation ($SpO_2$), carboxyhemoglobin (HbCO) and methemoglobin (HbMet). The monitor 302 may also be capable of storing or displaying historical or trending data related to one or more of the measured parameters or combinations of the measured parameters. The monitor 302 may also provide a trigger for the audible indictors 384, which operate beeps, tones and alarms, for example. Displays 382 include for example readouts, colored lights or graphics generated by LEDs, LCDs or CRTs to name a few. Audible indicators 384 include speakers or other audio transducers. User input devices 388 may include, for example, keypads, touch screens, pointing devices, voice recognition devices, or the like.

Figure 4:
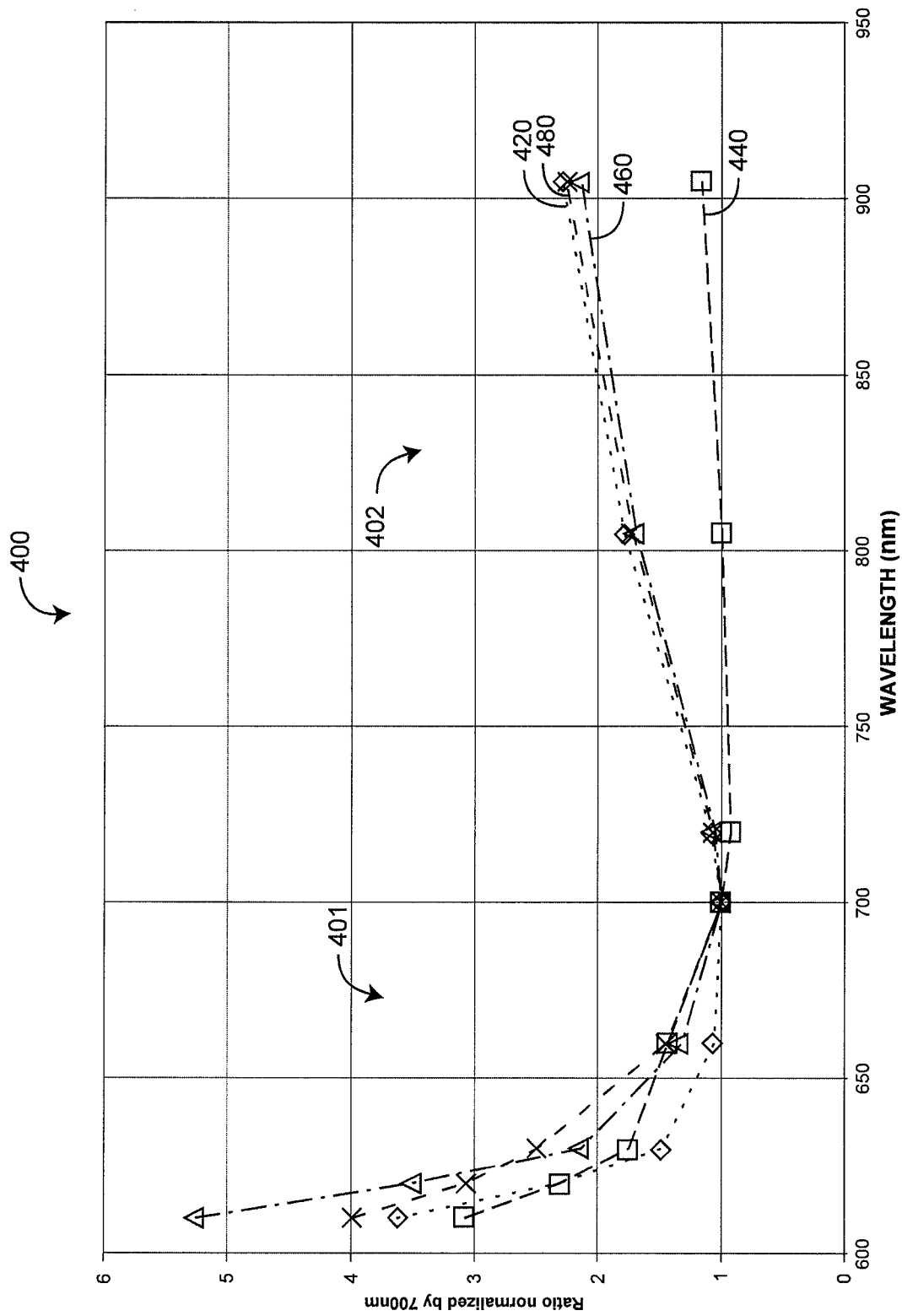
FIG. 4 is a graph of tissue profiles for high saturation, low saturation, high carboxyhemoglobin (HbCO) and high methemoglobin (MetHb)

FIG. 4 illustrates tissue profile curves 400, which are responsive to Hb constituents. In this example, the sensor emits eight wavelengths (610, 620, 630, 660, 700, 720, 805, 905 nm), which are normalized at 700 nm. Shown is a high saturation profile curve 420, e.g. SPO$_2$=100% (◇); a low saturation profile curve 440, e.g. SpO$_2$=70% (□); a high HbCO profile curve 460, e.g. HbCO=30% (Δ); and a high HbMet profile curve 480, e.g. HbMet=6% (X). The profile curves 420-480 each has a head portion 401 at wavelengths less than 700 nm and a corresponding tail portion 402 at wavelengths of greater than 700 nm. As shown in FIG. 4, a tissue profile head portion 401 has higher values when HbCO (Δ) or HbMet (X) has a higher percentage value. The head portion 401 has lower values when HbCO or HbMet has a lower percentage value. Also, both the head portion 401 and the tail portion 402 have higher values when SPO$_2$ is a high percentage (◇) and lower values when SPO$_2$ is a low percentage (□).

Figure 5:
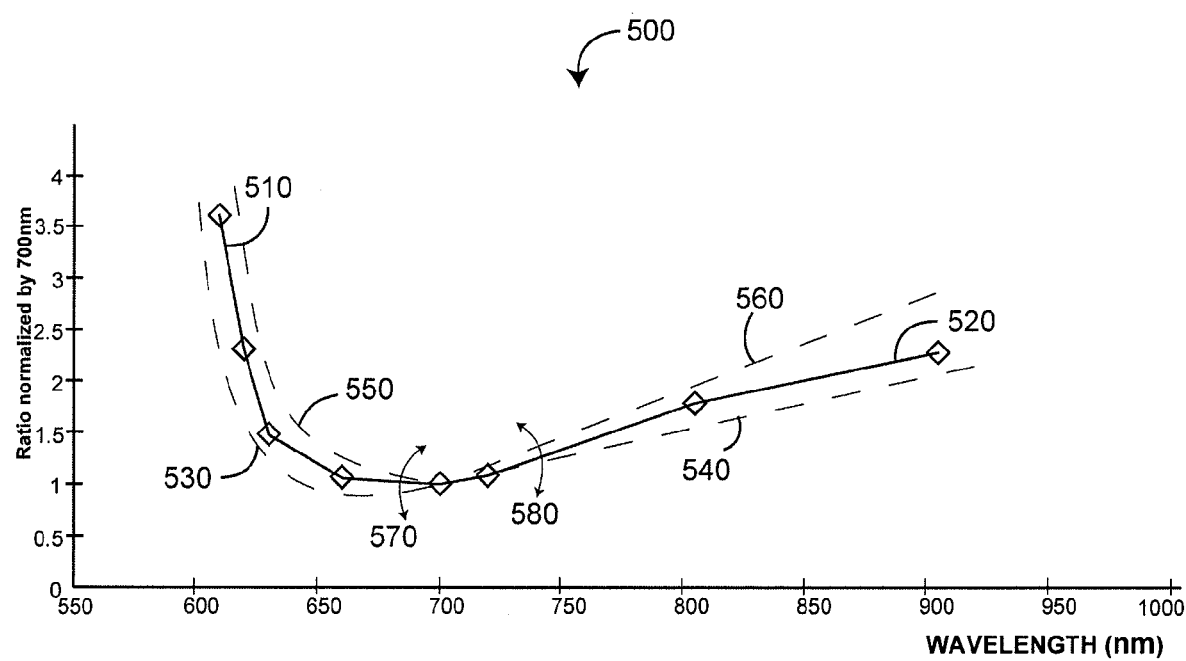
FIG. 5 is a graph illustrating tissue profile changes indicative of patient wellness.

FIG. 5 illustrates an example tissue profile 500 utilized as a wellness indicator. As described with respect to FIG. 4 above, the position or shape of the tissue profile or changes in the position or shape of the tissue profile provide an indication of patient wellness. In particular, position, shape or relative movements of the curve "head" 510 or the curve "tail" 520 or both indicate potentially detrimental values or changes in values of hemoglobin constituents. For example, a drop in the tissue profile head 510 or tail 520 below a predefined boundary 530, 540 may indicate reduced oxygen saturation. As another example, a rise in the tissue profile head 510 above a predefined boundary 550 may indicate increased concentrations of abnormal hemoglobin species, such as carboxyhemoglobin (HbCO) and methemoglobin (HbMet). Further, relative movements 570, 580 of the tissue profile 500 faster than a predefined rate may indicate potentially serious trends in the concentrations of normal or abnormal hemoglobin species.

Figure 1:
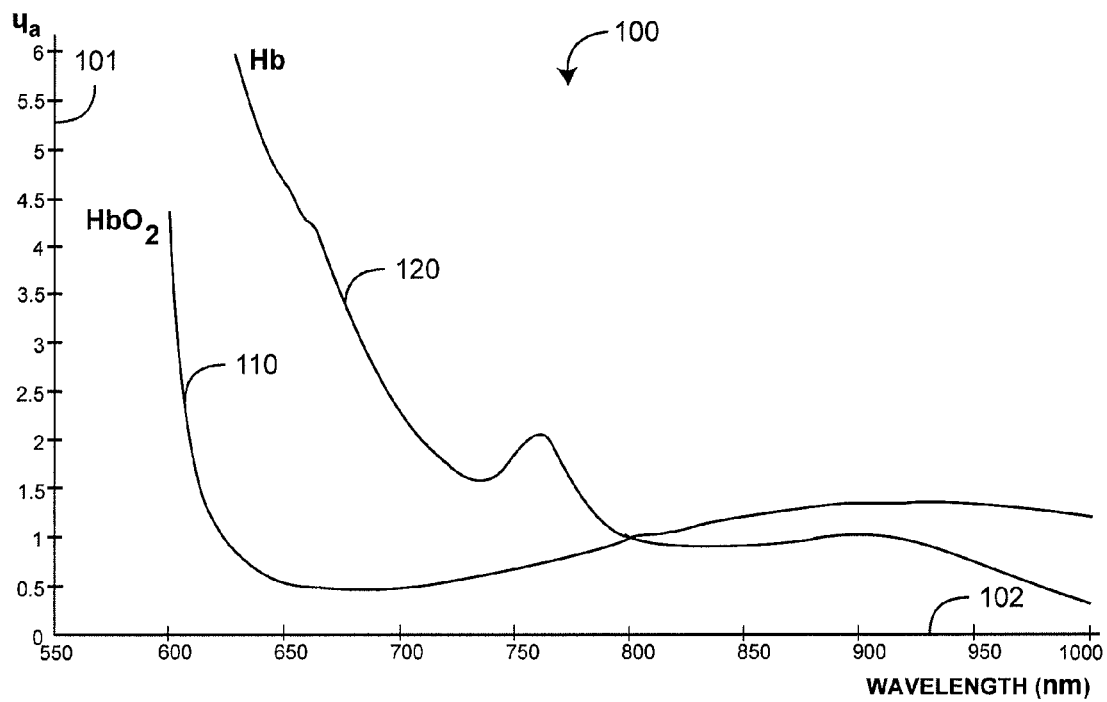
FIG. 1 is a graph of oxyhemoglobin and reduced hemoglobin light absorption versus wavelength across portions of the red and IR spectrum.
Figure 2:
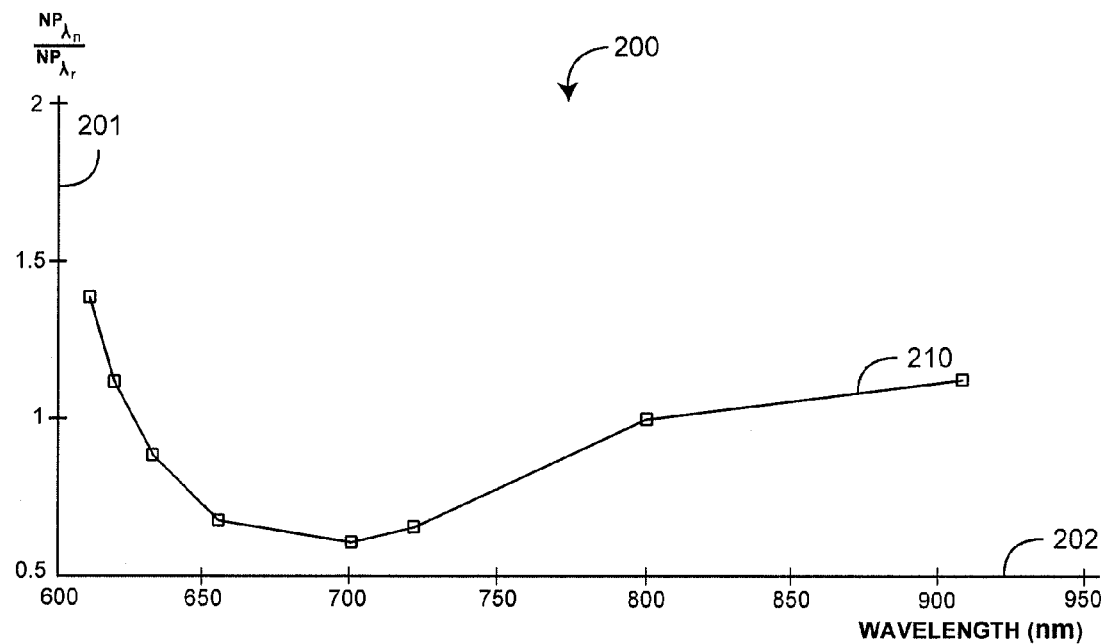
FIG. 2 is a graph of normalized plethysmograph (NP) ratios versus wavelength illustrating a tissue profile for 97% oxygen saturation.
Figure 6:
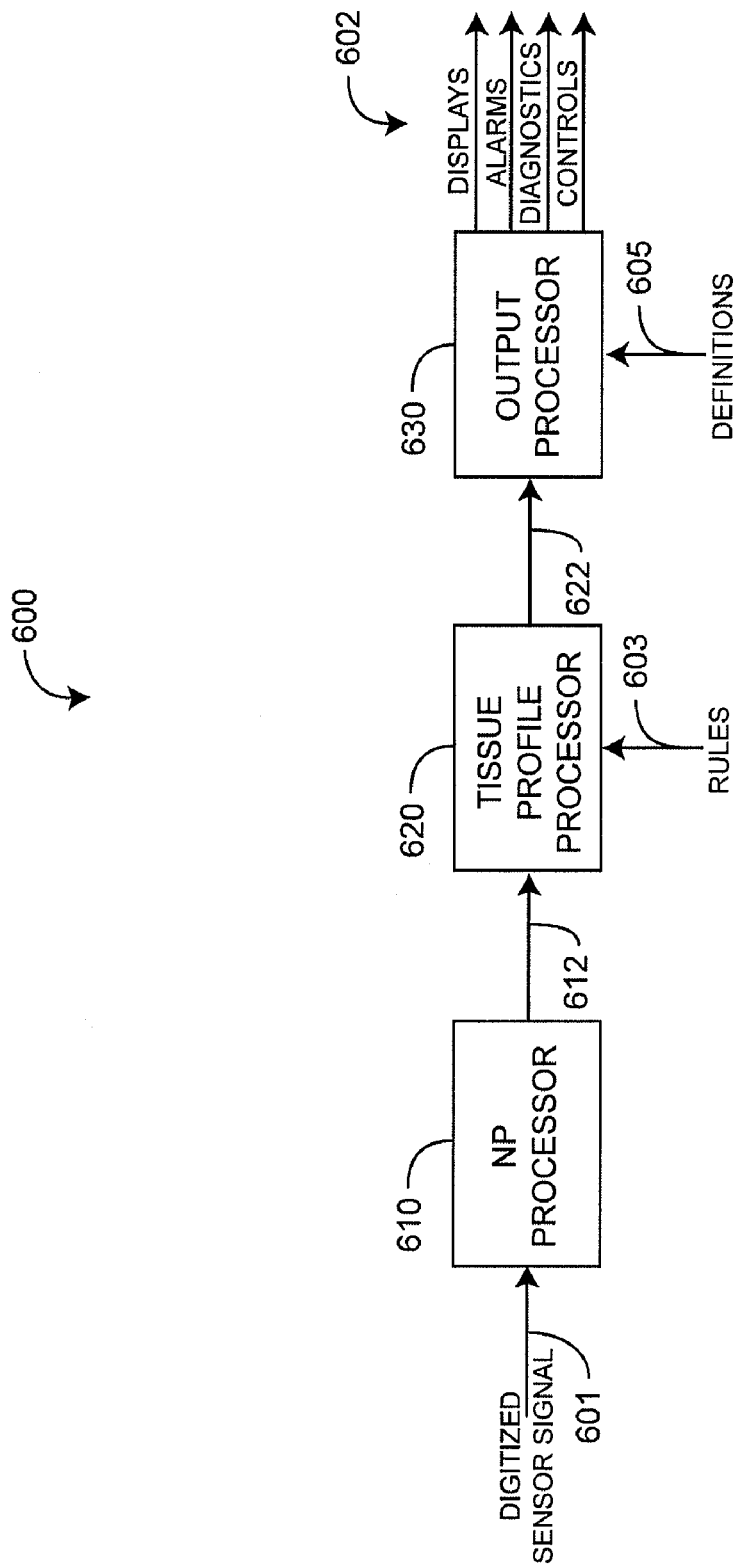
FIG. 6 is a block diagram of a tissue profile wellness monitor embodiment.

FIG. 6 illustrates a tissue profile wellness monitor 600 having a NP processor 610, a tissue profile processor 620 and an output processor 630. In an embodiment, these processors 610-630 execute in the DSP 340 (FIG. 3) to monitor tissue profile changes. The NP processor 610 has digitized sensor signal input 601 from one or more sensor channels, such as described with respect to FIG. 3, above, and generates normalized plethysmograph (NP) calculations 612 as described with respect to FIG. 1, above.

As shown in FIG. 6, the tissue profile processor 620 is configured to compare tissue profile changes 612 with respect to predetermined rules 603 and communicate the test results 622 to the output processor 630. As an example, the tissue profile processor 620 may communicate to the output processor 630 when a tissue profile portion changes faster than a predetermined rate.

Also shown in FIG. 6, the output processor 630 inputs the tissue profile processor results 622 and generates outputs 602 based upon predetermined output definitions 605. For example, if a test profile result is "true", it might trigger an audible alarm. Rules and corresponding outputs are described in further detail with respect to TABLE 1, below.

In an embodiment, the tissue profile wellness monitor 600 provides outputs 602 according to TABLE 1, below. The terms listed in TABLE 1 are described with respect to FIG. 6, above. Various other indicators, alarms, controls and diagnostics in response to various combinations of rules and output definitions can be substituted for, or added to, the rule-based outputs illustrated in TABLE 1.

In an embodiment, the tissue profile wellness monitor 600 grades a patient with respect to wellness utilizing green, yellow and red indicators. For example, a green panel light signals that the tissue profile is indicative of normal blood hemoglobin. A yellow panel light signals that changes in the tissue profile shape or position are indicative of potentially problematic changes in blood hemoglobin. A red panel light signals that the tissue profile is indicative of blood hemoglobin outside of normal ranges.

TABLE 1

Tissue Profile Rules and Outputs

| TISSUE PROFILE RULES | OUTPUTS |
|---|---|
| If all portions of tissue profile are within boundaries and relatively unchanging over time | Then illuminate green indicator. |
| If tail drops faster than tail trend limit; or head rises faster than head trend limit | Then illuminate yellow indicator |
| If tail or head are outside of boundaries | Then illuminate red indicator |

A tissue profile wellness monitor has been disclosed in detail in connection with various embodiments. These embodiments are disclosed by way of examples only and are not to limit the scope of the claims that follow. One of ordinary skill in art will appreciate many variations and modifications.

What is claimed is:

1. A physiological monitoring method comprising:
    emitting light of eight or more wavelengths into tissue of a patient, the eight or more wavelengths responsive to pulsatile blood flowing within the tissue of the patient;
    detecting the emitted light after attenuation by the tissue of the patient;
    continuously generating a tissue profile responsive to absorption of the emitted wavelengths using a processor in real time,
    continuously analyzing the tissue profile using the processor to determine if a change in the shape of the tissue profile has occurred;
    indicating a wellness condition of the patient based on the analysis of the tissue profile.

2. The physiological monitoring method according to claim 1 wherein generating comprises:
    measuring values at each of the emitted wavelengths; and
    defining values corresponding to at least a portion of a wavelength spectrum between the emitted wavelengths based upon known characteristics of the tissue site.

3. The physiological monitoring method according to claim 2 wherein analyzing comprises:
    setting a limit corresponding to the tissue profile; and
    specifying an output corresponding to a comparison of the tissue profile to the set limit.

4. The physiological monitoring method according to claim 3 wherein indicating comprises generating at least one of a display, an alarm, diagnostic and a control.

5. The physiological monitoring method according to claim 3 wherein the setting a limit comprises defining at least one of a boundary and a maximum rate of change for at least a portion of the tissue profile.

6. The physiological monitoring method according to claim 5 wherein the indicating comprises generating at least one of an audible and visual alarm in response to at least a portion of the tissue profile exceeding the set limit.

7. The physiological monitoring method according to claim 2 wherein the measuring comprises calculating a normalized plethysmograph (NP) for each of the emitted wavelengths with respect to the NP at one of the emitted wavelengths.

8. A physiological monitoring method comprising:
    emitting optical radiation of three or more wavelengths into the tissue of a patient;

detecting the optical radiation after attenuation of the light by the tissue of the patient;

continuously measuring a normalized plethysmograph (NP) at each of multiple wavelengths of the optical radiation so as to generate a tissue profile, the NP being responsive to attenuation of the optical radiation by constituents of pulsatile blood flowing within a tissue site illuminated by the optical radiation;

analyzing the tissue profile to determine if the shape of the tissue profile indicates an abnormal condition of the patient; and outputting at least one of a display, alarm, diagnostic and control according to the testing results.

9. The physiological monitoring method according to claim 8 wherein analyzing comprises:

dividing the profile into a head portion at wavelengths less than a normalizing wavelength and a tail portion at wavelengths greater than a normalizing wavelength; and evaluating the tail portion separately from the head portion.

10. The physiological monitoring method according to claim 9 wherein the evaluating comprises:

comparing the head portion against a head boundary; and comparing the tail portion against a tail boundary.

11. The physiological monitoring method according to claim 10 wherein the evaluating comprises:

comparing the head portion against a head trend limit; and comparing the tail portion against a tail trend limit.

12. The physiological monitoring method according to claim 11 wherein outputting comprises:

activating a first signal indicative of normalcy so long as the head portion is within the head boundary and changing less than the head trend limit and the tail portion is within the tail boundary and changing less than the tail trend limit;

activating a second signal indicative of caution when at least one of the head portion is changing faster than the head trend limit and the tail portion is changing faster than the tail trend limit; and activating a third signal indicative of high alert when at least one of the head portion is outside the head boundary and the tail portion is outside the tail boundary.

13. A physiological monitoring method comprising:

emitting three or more wavelengths of light into a tissue site of a patient including pulsating blood;

detecting the light after attenuation by the tissue site;

measuring a physiological parameter responsive to multiple wavelengths of optical radiation after attenuation by constituents of pulsatile blood flowing within a tissue site;

continuously generating a tissue profile in response to the physiological parameter using a processor;

defining shape change limits for at least a portion of the tissue profile; and indicating when the tissue profile changes shape and exceeds the defined limits.

14. The physiological monitoring method according to claim 13 wherein the defining limits comprise setting for at least a portion of the tissue profile at least one of a boundary and a trend limit.

15. The physiological monitoring method according to claim 14 further comprising:

determining a normalizing wavelength so as to divide the tissue profile into a first portion at wavelength of less than the normalizing wavelength and a second portion at wavelength of greater than the normalizing wavelength; and defining limits for each of the first portion and the second portion.

16. The indicator method according the claim 15 wherein said normalized wavelength is 700 nm.

* * * * *